United States Patent
Kim et al.

(10) Patent No.: US 7,288,652 B2
(45) Date of Patent: Oct. 30, 2007

(54) METHOD FOR PREPARING OLTIPRAZ

(75) Inventors: Jin Wan Kim, Seoul (KR); Kwang Do Choi, Anyang (KR); Jee Woong Lim, Gunpo (KR); Kwang Hyeg Lee, Sungnam (KR); Sang Ho Lee, Anyang (KR)

(73) Assignee: CJ Corporation, Seoul (KR)

( * ) Notice: Subject to any disclaimer, the term of this patent is extended or adjusted under 35 U.S.C. 154(b) by 232 days.

(21) Appl. No.: 10/536,492

(22) PCT Filed: Nov. 25, 2003

(86) PCT No.: PCT/KR03/02552

§ 371 (c)(1),
(2), (4) Date: May 25, 2005

(87) PCT Pub. No.: WO2004/048369

PCT Pub. Date: Jun. 10, 2004

(65) Prior Publication Data

US 2006/0106079 A1    May 18, 2006

(30) Foreign Application Priority Data

Nov. 26, 2002  (KR) ...................... 10-2002-0074119

(51) Int. Cl.
*C07D 401/00*  (2006.01)
*C07D 405/00*  (2006.01)
*C07D 403/00*  (2006.01)
*C07D 409/00*  (2006.01)
*C07D 411/00*  (2006.01)

(52) U.S. Cl. .................................... 544/405

(58) Field of Classification Search ..................... None
See application file for complete search history.

(56) References Cited

U.S. PATENT DOCUMENTS 4,110,450 A    8/1978  Barreau et al.
2003/0191137 A1   10/2003  Kim et al.

FOREIGN PATENT DOCUMENTS

WO    WO 01/09118 A2    2/2001

OTHER PUBLICATIONS

Kugucheva et al, "Gas-Chromatographic Analysis of Trace Impurities for Ethylbenzene, o-, m- and p-xylenes in Toluene" Neftepererabotka i Neftekhimiya, vol. 3, pp. 35-36 (1983). As Abstracted by Caplus.*
Iida and Okada "Determination of Trace Impurities in Toluene by Gas Chromatography-Chemical Ionization Mass Spectrometry" Bunseki Kagaku, vol. 26(9), pp. 630-634 (1977). As Abstracted by Caplus.*
Hogfeldt, E. "Impurities in Analytical Reagent Grade Chemicals" Journal of Chromatography, vol. 12(1), pp. 112-113 (1963).*
Kugucheva et al, "Gas-Chromatographic Analysis of Trace Impurities for Ethylbenzene, o-, m- and p-xylenes in Toluene" Neftepererabotka i Neftekhimiya, vol. 3, pp. 35-36 (1983) Russian-Language Version and English Translation.*
Iida and Okada "Determination of Trace Impurities in Toluene by Gas Chromatography-Chemical Ionization Mass Spectrometry" Bunseki Kagaku, vol. 26(9), pp. 630-634 (1977) Japanese-Language Version and English Translation.*
Abdaly F., et al., "Synthesis and schistosomicidal activity of 4-methyl-5(aryl vinyl)-1,2-dithiole-3-thiones", *IL Farmaco*, 1991, pp. 45-62, vol. 46(1).
Chi W.J., et al., "Oltipraz, a novel inhibitor of hepatitis B virus transcription through elevation of p53 protein", *Carcinogenesis*, 1998, pp. 2133-2138, vol. 19(12).
Curphey T.J., "A superior procedure for the conversion of 3-oxoesters to 3 *H*-1,2-dithiole-3-thiones",*Tetrahedron Letters*, 2000, pp. 9963-9966, vol. 41.
Curphey T.J., et al., "A new synthesis of 3H-1,2-Dithiole-3-thiones", *Tetrahedron Letters*, 1993, pp. 3703-3706, vol. 34(23).
Vaccher C., et al., Preparation and schistosomicidal activity of vinylogues of 1,3-dithio-3-thione, *IL Farmaco*, 1987, pp. 397-407, vol. 42(6).

* cited by examiner

*Primary Examiner*—Zachary C Tucker
(74) *Attorney, Agent, or Firm*—Rothwell, Figg, Ernst & Manbeck

(57) ABSTRACT

Provided is a method for preparing oltipraz. The method includes reacting methyl 2-methyl-3-(pyrazin-2-yl)-3oxo-propionate with phosphorus pentasulfide in the presence of a mixed solvent of toluene and xylene, followed by recrystallization.

8 Claims, No Drawings

METHOD FOR PREPARING OLTIPRAZ

CROSS REFERENCE TO RELATED APPLICATION

This application is a 35 U.S.C. § 371 National Phase Entry Application from PCT/KR03/002552, filed Nov. 25, 2003, and designating the U.S.

BACKGROUND OF THE INVENTION

1. Field of the Invention

The present invention relates to a method for preparing oltipraz represented by Formula 1 below:

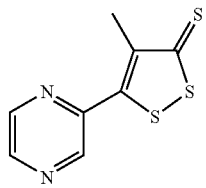

Formula 1

2. Description of the Related Art

Oltipraz represented by Formula 1 above was originally developed as an anti-schistosomal drug that eliminates parasites known blood flukes by Rhone-Poulenc, in 1980. However, during clinical trials, it was found that oltipraz does not have excellent drug effect relative to praziquantel that had been currently used for the treatment of parasite infections, and thus oltipraz was later abandoned.

Thereafter, in studies on a new reaction mechanism of oltipraz conducted in the 1990s, it was reported that oltipraz is effective for the inhibition of HIV propagation [Prochaska et al., 1995], the prevention and treatment of cancers, and the inhibition of HBV transcription [Chi et al., 1998].

Methods for preparing oltipraz are disclosed in U.S. Pat. No. 4,110,450, assigned to Rhone-Poulenc, issued in 1978. This patent provides two methods for preparing oltipraz, one of which is as following Scheme 2.

Scheme 2

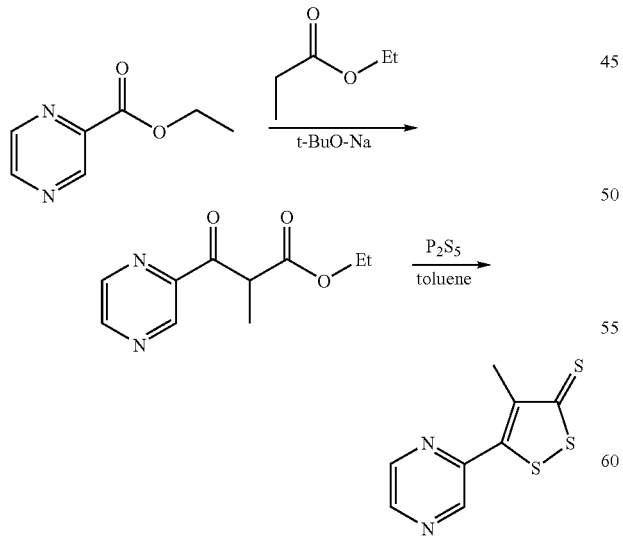

According to Scheme 2, however, the duration for preparation of oltipraz is too long, as 18 to 24 hours. Also, after a Claisen condensation reaction between ethyl pyrazine-2-carboxylate and ethyl propionate, separation and purification using a column are done. Furthermore, a total yield achieved after two steps of Scheme 2 above is 4.2%, which is too low for mass production.

Another method for preparing oltipraz disclosed in the above patent is as following Scheme 3.

Scheme 3

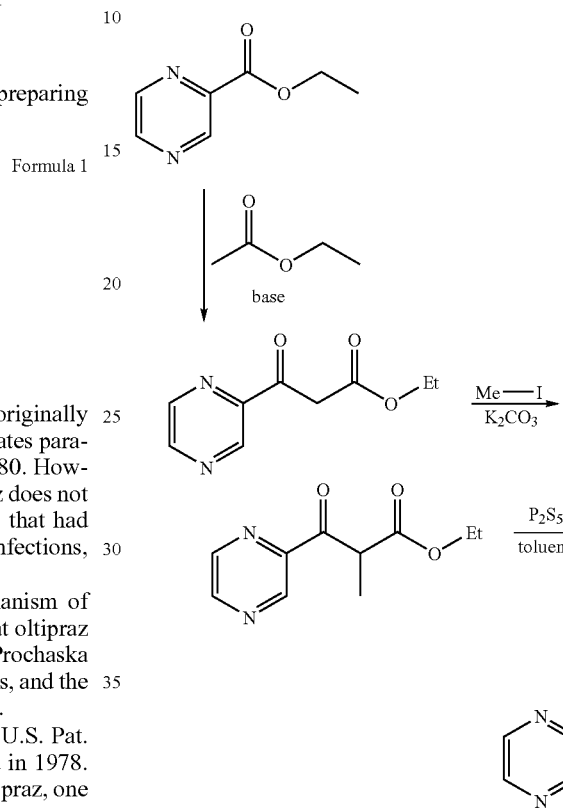

The method of Scheme 3 includes an additional reaction step, as compared to the method of Scheme 2. Like in Scheme 2, a total yield is too low for mass production.

WO01/09118, issued on August 2001, discloses a method for preparing oltipraz as following Scheme 4:

Scheme 4

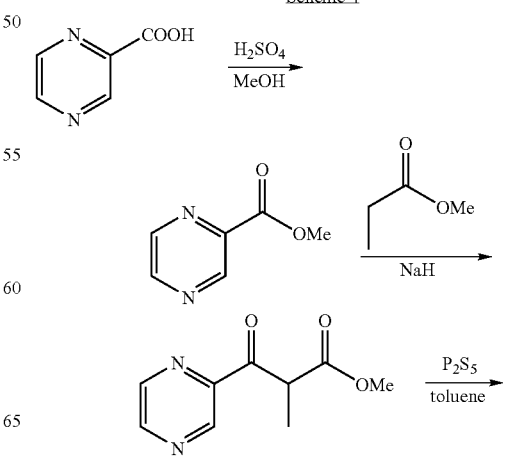

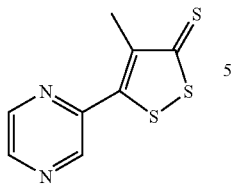

In the above method, since sodium hydride is used as a base in a Claisen condensation reaction, there is an explosion risk of hydrogen produced during the condensation reaction. Also, since sodium hydride dispersed in oil is used, a pretreatment for oil removal is required. In particular, excess phosphorus pentasulfide ($P_2S_5$) inevitably used in the formation of a dithiolethione ring may cause severe environmental contamination. In addition, like in the above-described methods, a lengthy reaction duration is required.

Steps influencing the total yield of oltipraz in oltipraz preparation methods are a Claisen condensation reaction step in the presence of strong base and a dithiolethione ring formation step using $P_2S_5$.

In formation of dithiolethione rings from 3-oxoester compounds, a method of enhancing the yield of dithiolethione using various reagents such as $P_2S_5$, Lawesson's reagent, sulfur (S)/$P_2S_5$, or hexamethyldisiloxane/$P_2S_5$ has been reported [Tetrahedron Letters 2000, p. 9965, 17-18]. However, the yield of 3-oxoester compounds with a nitrogen-containing hetero ring is very low, and in particular, the yield of oltipraz with a pyrazinyl group is extremely low, as less than 10%.

SUMMARY OF THE INVENTION

Therefore, while searching for solutions to the above problems, the present inventors developed a novel method for preparing oltipraz in which a 3-oxoester compound can be produced in high yield in the presence of a strong base with no explosion risk, and the duration for formation of a dithiolethiole ring is significantly reduced, and completed the present invention.

The present invention provides a method for preparing oltipraz.

DETAILED DESCRIPTION OF THE INVENTION

The present invention provides a method for preparing oltipraz represented by Formula 1, including reacting methyl 2-methyl-3-(pyrazin-2-yl)-3-oxopropionate represented by Formula 4 with phosphorus pentasulfide ($P_2S_5$) in the presence of a mixed solvent of toluene and xylene, followed by recrystallization.

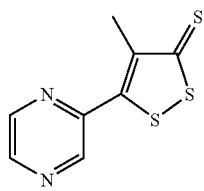

Formula 1

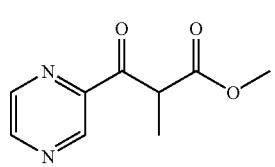

Formula 4

Preferably, the volume ratio of toluene to xylene in the mixed solvent is in a range of 1:1 to 1:4.

Since the mixed solvent of toluene and xylene has a high boiling point, a reflux temperature can be efficiently increased. The activity of $P_2S_5$ increases with increasing reaction temperature. This is supported by the results of experiments using toluene, xylene, tetrahydrofuran, or methylenechloride, that as a reaction temperature increases, the activity of $P_2S_5$ increases. In this regard, the use of the mixed solvent of toluene and xylene can increase a reaction yield.

Also, due to the use of the mixed solvent, the reaction duration for formation of dithiolethione is reduced to 4 to 6 hours, which is time effective. This is in contrary to a conventional method requiring 18 to 24 hours for the formation of dithiolethione.

Preferably, $P_2S_5$ is used in an amount of 0.5 to 3 equivalents, more preferably, 1.05 to 1.50 equivalents, based on 1 equivalent of methyl 2-methyl-3-(pyrazin-2-yl)-3-oxopropionate.

The methyl 2-methyl-3-(pyrazin-2-yl)-3-oxopropionate of Formula 4 may be produced by a Claisen condensation reaction between methyl pyrazine-2-carboxylate represented by Formula 3 below and methyl propionate in the presence of a strong base.

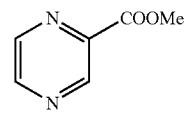

Formula 3

The strong base may be sodium hydroxide, potassium hydroxide, sodium t-butoxide, potassium t-butoxide, or sodium amide. Potassium t-butoxide is preferred.

A solvent that can be used in the condensation reaction is a nonreactive solvent commonly used in an organic reaction, i.e., toluene, methylenechloride, or tetrahydrofuran. Tetrahydrofuran is preferred.

A conventional method includes a separation and/or purification step after the Claisen condensation reaction, or another additional reaction step, which creates commercial inefficiency. However, under the above-described optimal reaction condition, a high purity product can be obtained even when a separation and/or purification process is not used. Also, a single solvent can be reused after distilled, thereby contributing to cost curtailment effect.

Preferably, the strong base is used in an amount of 1.5 to 2.5 equivalents, more preferably, 1.8 to 2.0 equivalents, based on 1 equivalent of methyl pyrazine-2-carboxylate.

The methyl pyrazine-2-carboxylate of Formula 3 may be produced by an esterification reaction of pyrazine-2-carboxylic acid represented by Formula 2 below in a methanol solution in the presence of an acid catalyst such a sulfuric acid under reflux.

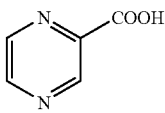

Formula 2

In the esterification reaction, it was found that the amount of an acid catalyst is closely related to a reaction duration. Through studies on increase or decrease of the amount of an impurity, which is a byproduct, with increasing the amount of an acid catalyst, the present inventors found that an increase of the amount of an acid catalyst enables to a reduction of a reaction duration without producing an impurity, which increases a production efficiency relative to the prior art.

The acid catalyst that can be used in the esterification reaction is an inorganic acid commonly commercially available, for example, sulfuric acid, hydrochloric acid, or phosphoric acid. The most preferable acid catalyst is sulfuric acid. Due to an increase of the amount of the acid catalyst, pyrazine-2-carboxylate can be obtained without an increase of an impurity by reflux of 4 to 5 hours, which is in contrary to a conventional reflux time of 48 hours. Preferably, the amount of the acid catalyst is in a range of $5.8 \times 10^{-3}$ to $25.0 \times 10^{-3}$ equivalents, based on 1 mole of methyl pyrazine-2-carboxylic acid.

The overall reaction of the above-described method for preparing oltipraz can be summarized as follows.

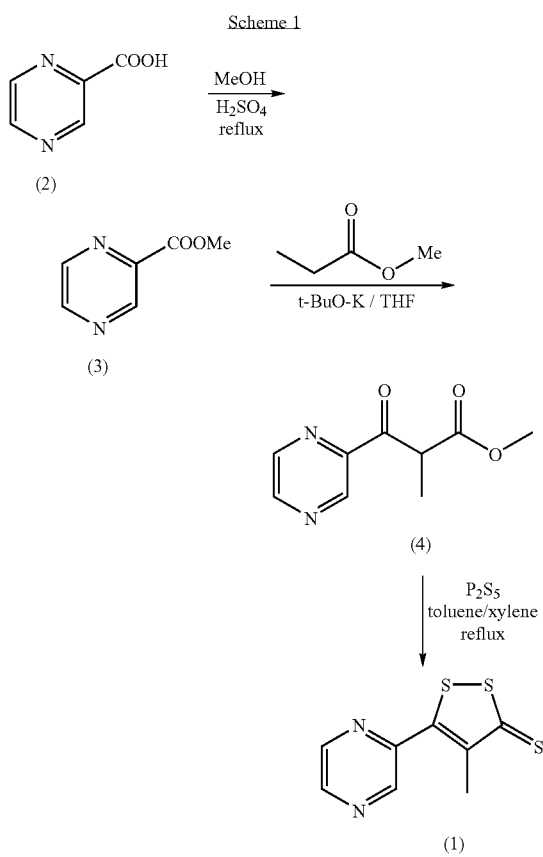

After all the reactions are completed, an oltipraz crude crystal is obtained as a final product. A crystallization solvent for the oltipraz crude crystal may be methanol, ethanol, ethylacetate, or acetonitrile. The most preferable crystallization solvent is methanol.

The oltipraz crude crystal may be purified using a recrystallization solvent selected from the group consisting of acetonitrile, methanol, N,N-dimethylformamide, N,N-dimethylacetamide, and a mixed solvent thereof.

When the recrystallization solvent is acetonitrile, it is preferable to use 30 to 40 parts by volume of acetonitrile, based on 1 part by weight of the oltipraz crude crystal.

When the recrystallization solvent is a mixed solvent of N,N-dimethylformamide and acetonitrile, it is preferable to use 15 to 20 parts by volume of N,N-dimethylformamide and 30 and 40 parts by volume of acetonitrile, based on 1 part by weight of the oltipraz crude crystal.

When the recrystallization solvent is a mixed solvent of N,N-dimethylformamide and methanol, it is preferable to use 15 to 20 parts by volume of N,N-dimethylformamide and 30 to 40 parts by volume of methanol, based on 1 part by weight of the oltipraz crude crystal.

If the amount of the recrystallization solvent is outside the above range, the yield of a product significantly reduces. Also, the recrystallization solvent may be remained in the product.

Hereinafter, the present invention will be described more specifically by examples. However, the following examples are provided only for illustrations and thus the present invention is not limited to or by them.

EXAMPLE 1

Methyl pyrazine-2-carboxylate (Formula 3)

20.0 g (805.8 mmole) of pyrazine-2-carboxylic acid was added to 160 mL of methanol, and 1.0 mL of a concentrated sulfuric acid was gradually dropwise added thereto with stirring. A reaction solution was refluxed at a temperature of 80 to 85° C. for 5 hours. The reaction solution was cooled to a temperature of 20 to 22° C. and concentrated to a volume of 25 mL. Then, 80 mL of methylenechloride and 40 mL of water were added to the resultant concentrate. The resultant solution was then neutralized by gradual addition of 40 mL of a saturated sodium hydrogen carbonate solution to get a pH of 8.5. An organic layer was separated and a water layer was extracted again with 40 mL of methylenechloride. The combined organic layer was dried over anhydrous magnesium sulfate, filtered, and washed with 20 mL of methylenechloride. A filtrate was concentrated to give 21.1 g of the titled compound as a pale brown solid (yield 94.8%).

Melting point: 60~61° C.

EXAMPLE 2

Methyl 2-methyl-3-(pyrazin-2-yl)-3-oxopropionate (Formula 4)

1.2 L of tetrahydrofuran and 87.8 g (0.78 mole) of potassium t-butoxide were added to a reactor and cooled to 0° C. 71.5 mL (0.74 mol) of methyl propionate was dropwise added to the reactor and stirred at 0° C. for 30 minutes. 60 g (0.434 mole) of the methyl pyrazine-2-carboxylate of Example 1 dissolved in 500 mL of tetrahydrofuran was dropwise added to the reactor for 30 minutes and stirred at a temperature of 20 to 25° C. for 3 hours. 0.5 L of distilled water and 0.5 L of saturated ammonium chloride solution were added to the reaction solution and stirred for 30 minutes. The resultant reaction solution was concentrated to a volume of 1.0 L and then extracted with 1.0 L of methylenechloride. The resultant extract was dried over anhydrous magnesium sulfate and filtered. The filtrate was concentrated to give 75.0 g of the titled compound as a dark brown viscous oil (yield 89.0%).

NMR($\delta$, CDCl$_3$): 1.50(d, 3H), 3.65(s, 3H), 4.70(q, 1H), 8.60(d, 1H), 8.80(d, 1H), 9.21(s, 1H)

EXAMPLE 3

Synthesis and Recrystallization of Oltipraz 300 mL of toluene, 350 mL of xylene, and 48.0 g (216 mmole) of phosphorus pentasulfide were added to a reactor and heated to a temperature of 120 to 122° C. 40.0 g (206 mmole) of methyl 2-methyl-3-(pyrazin-2-yl)-3-oxopropionate prepared in Example 2 was dissolved in 100 mL of toluene and then dropwise added to the reactor. The reaction solution was allowed to proceed under reflux at 135° C. for 4 hours and then cooled to 20° C. After addition of 500 mL of distilled water and 500 mL of methanol, the pH of the resultant reaction solution was adjusted to 8.5 with adding a 28% ammonia solution (about 51 mL). An organic layer was separated, dried over anhydrous magnesium sulfate, filtered, and concentrated under reduced pressure. 150 mL of methanol was added to the resultant concentrate, stirred for one hour, and filtered. A filtrate was washed with 100 mL of methanol to give a humid oltipraz crude crystal (12.0 to 13.0 g).

The oltipraz crude crystal was placed in a reactor. 400 mL of acetonitrile was added and dissolved at 80° C. 1.4 g of activated carbon was added and stirred for 30 minutes. The resultant solution was filtered, washed with 100 mL of acetonitrile, crystallized with stirring at a temperature of 20 to 25° C. for 2 hours, and again stirred at 10° C. for one hour. The obtained crystal was filtered, washed with 20 mL of acetonitrile, and vacuum dried at 40° C. to give 6.37 g of oltipraz (13.6% yield, >99.5% purity).

NMR($\delta$, CDCl$_3$): 2.51(s, 3H), 8.70(d, 1H), 8.80(d, 1H), 9.21(s, 1H)

EXAMPLE 4

Recrystallization of Oltipraz

An oltipraz crude crystal prepared in the same manner in Example 3 and 180 mL of N,N-dimethylformamide were placed in a reactor and dissolved at 80° C. Then, 1.4 g of activated carbon was added and stirred for 30 minutes. The resultant solution was filtered and washed with 20 mL of N,N-dimethylformamide. 360 mL of acetonitrile was dropwise added at 80° C., crystallized with stirring at 20 to 25° C. for 2 hours, and again stirred at 10° C. for one hour. The resultant crystal was filtered, washed with 20 mL of acetonitrile, and vacuum dried at 40° C. to give 7.15 g of oltipraz (15.6% yield, >99.6% purity).

NMR($\delta$, CDCl$_3$): 2.51(s, 3H), 8.70(d, 1H), 8.80(d, 1H), 9.21(s, 1H)

EXAMPLE 5

Recrystallization of Oltipraz

An oltipraz crude crystal prepared in the same manner in Example 3 and 180 mL of N,N-dimethylformamide were placed in a reactor and dissolved at 80° C. Then, 1.4 g of activated carbon was added and stirred for 30 minutes. The resultant solution was filtered and washed with 20 mL of N,N-dimethylformamide. 360 mL of methanol was dropwise added at 80° C., crystallized with stirring at 20 to 25° C. for 2 hours, and again stirred at 10° C. for one hour. The resultant crystal was filtered, washed with 20 mL of methanol, and vacuum dried at 40° C. to give 7.53 g of oltipraz (16.1% yield, >99.6% purity).

NMR($\delta$, CDCl$_3$): 2.51(s, 3H), 8.70(d, 1H), 8.80(d, 1H), 9.21(s, 1H).

According to an oltipraz preparation method of the present invention, there exists no explosion risk of hydrogen produced and a reaction duration is reduced. In addition, impurity separation and purification processes in the interim reaction process are not required, thereby ensuring the economical mass production of oltipraz.

What is claimed is:

1. A method for preparing oltipraz, comprising reacting methyl 2-methyl-3-(pyrazin-2-yl)-3-oxopropionate with phosphorus pentasulfide in the presence of a mixed solvent of toluene and xylene under reflux to produce an oltipraz crude crystal, followed by recrystallization, wherein a volume ratio of toluene to xylene in the mixed solvent is in a range of 1:1 to 1:4.

2. The method of claim 1, wherein the methyl 2-methyl-3-(pyrazin-2-yl)-3-oxopropionate is prepared by condensation reaction of methyl pyrzaine-2-carboxylate and methyl propionate in the presence of a strong base.

3. The method of claim 2, wherein the strong base is potassium t-butoxide.

4. The method of claim 2, wherein a solvent for the condensation reaction is tetrahydrofuran.

5. The method of claim 1, wherein a solvent for the recrystallization is selected from the group consisting of acetonitrile, methanol, N,N-dimethylformamide, N,N-dimethylacetamide, and a mixed solvent thereof.

6. The method of claim 5, wherein acetonitrile in an amount of 30 to 40 parts by volume, based on 1 part by weight of the oltipraz crude crystal, is used for the recrystallization.

7. The method of claim 5, wherein a mixed solvent of N,N-dimethylformamide in an amount of 15 to 20 parts by volume and acetonitrite in an amount of 30 to 40 parts by volume, based on 1 part by weight of the oltipraz crude crystal, is used for the recrystallization.

8. The method of claim 5, wherein a mixed solvent of N,N-dimethylformamide in an amount of 15 to 20 parts by volume and methanol in an amount of 30 to 40 parts by volume, based on 1 part by weight of the oltipraz crude crystal, is used for the recrystallization.

* * * * *